United States Patent [19]
Trippi

[11] 4,444,179
[45] Apr. 24, 1984

[54] ORTHOPEDIC TONGS

[76] Inventor: Anthony C. Trippi, P.O. Box 4309, San Luis Obispo, Calif. 93403

[21] Appl. No.: 239,214

[22] Filed: Mar. 2, 1981

[51] Int. Cl.³ .............................................. A51F 5/04
[52] U.S. Cl. .................................................... 128/75
[58] Field of Search .................................... 128/68–69, 128/75–76, 84 R, 84 C, 85, 87, DIG. 23, 71, 92; 177/250

[56] References Cited

U.S. PATENT DOCUMENTS

| 1,921,436 | 8/1933 | Strachan | 177/250 |
| 2,166,229 | 7/1939 | Anderson | 128/75 |
| 2,494,792 | 1/1950 | Bloom | 128/92 |
| 2,494,792 | 1/1950 | Bloom | 128/92 |
| 3,604,412 | 9/1974 | Gardner | 128/75 |
| 3,923,046 | 12/1975 | Heifetz | 128/75 |
| 3,957,040 | 5/1976 | Calabrese | 128/75 |

FOREIGN PATENT DOCUMENTS

| 622199 | 11/1935 | Fed. Rep. of Germany | 272/DIG. 4 |
| 140162 | 1/1961 | U.S.S.R. | 128/DIG. 23 |
| 633526 | 8/1976 | U.S.S.R. | |

Primary Examiner—C. Fred Rosenbaum
Assistant Examiner—Sherri E. Vinyard
Attorney, Agent, or Firm—Christie, Parker & Hale

[57] ABSTRACT

A cervical traction tong having three or more skull pins for rigid attachment to the head of a spinal-fracture patient. The tong includes a movable attachment member for anchoring a tension line at a variety of angulations enabling adjustment of the tension-line force vector in fore-and-aft and side-to-side directions. Connectors are adjustably fitted at opposite lower ends of the tong for coupling to fixation rods extending from a body cast or vest, and thereby permitting an easy and controlled transition from tension line to fixation rods as a source of tension force acting on the head.

1 Claim, 6 Drawing Figures

ORTHOPEDIC TONGS

TECHNICAL FIELD

This invention relates to cervical skeleton traction tongs useful in the treatment of the unstable spine.

BACKGROUND ART

Cervical skeleton traction is used exclusively to treat the unstable spine. It is also sometimes used in treating signal fractures and to accomplish reduction of cervical facet dislocations. In the past, skeleton traction has been applied utilizing caliper-like devices and halo-type rings. Both types of devices use pins which are drilled or screwed through the scalp into the skull to allow force vectors to be applied to the skull and spinal structure.

Exemplary of the caliper devices of the prior art are the Crutchfield Tongs. This device was in the shape of an "X" and was pivoted at the intersection of the two arms. At the scalp end of each arm, a pin was affixed for penetration into pre-drilled skull holes. At the other end of each arm, there was a threaded rod and thumb screw structure which, when operated, tended to force the pin ends of the tong arms together or apart in accordance with the direction in which the thumb screw was turned. These tongs were applied to the top of the head with one pin on each side of the longitudinal axis of the spine. The pins were roughly perpendicular to the scalp, but because the tongs did not reach down around the head to a point just above the ears, the angle of the scalp pins to the longitudinal axis of the spine was acute when viewed from the front or rear of the head. Accordingly, when tension was placed upon the Crutchfield Tongs, the angle of the pins was such that, if not tightly compressed by the thumb screw, it was possible to pull the Crutchfield Tongs completely out of the skull.

Only two pins were used in the Crutchfield Tongs. As a result, a pivot line was established between the contact points of the pivot points and the skull. Thus, flexion and extension of the skull in relation to the spine, i.e., tilting of the head forward and rearward, was not possible with the Crutchfield Tongs. Further, traction using the Crutchfield Tongs confined the patient to bed such that ambulation was not possible.

Another example of caliper devices are Barton's tongs. The structure of Barton's tongs was similar to that of the Crutchfield device; however, the arms are longer such that the pins reach further down on the head toward the ear. The shape and length of the tong arms was such that the drills of Barton's tongs entered the skull horizontally at a point somewhere between the top of the head and the ear, such that a 90° angle was formed with the longitudinal axis of the spine. Barton's tongs had a greater resistance to pulling out of the skull than did Crutchfield's tongs, because of the increased angles of the pins with respect to the spine.

Another example of this type of device is the Gardner tongs which had a different structure than the Crutchfield tongs and were less likely to loosen under prolonged traction load than were Crutchfield's tongs. Gardner's tongs were a semicircular frame structure in the approximate shape of a horseshoe with threaded pin holes on each end of the horeshoe arms. The horseshoe was placed down over the patient's head such that the pins contacted the skull at a point just above the ears and in line with the longitudinal axis of the spine. Thus the plane defined by the two pins and the point of contact of the tongs with the traction line passed through the center line of the spine. Excessive anterior placement of the tongs resulted in a forward tilt of the head resulting in misalignment of the spine. Since only two pins were used, a pivot line was formed and it was not possible to apply flexion and extension force vectors in the anterior-posterior plane with this device.

Anterior-posterior positioning of pins was disclosed in Russian Pat. No. 633,526. That patent discloses a tong-like device with facility for affixing two pins on either side of the head. This patent also discloses a plurality of holes centered at the top of the horseshoe and spaced about its center line. This feature plus the four points of contact with the skull allowed the skull to be canted from left to right by placing the hook of a traction line to the left or right of the centerline of the horseshoe.

The inconvenience and attendant additional risk of confining a patient to bed during extended traction resulted in the development of the halo-type device. The halo device consisted of a circular frame with an upturned portion in the rear, said frame completely encircling the skull. Several pins were used to engage the skull, resulting in increased ability to control the force vectors of the traction force. Force was applied to the halo ring by means of two hooks which attached to the halo ring on either side of the head in line with the longitudinal axis of the spine. These hooks could be moved forward or rearward to control flexion and extension torques on the skull in the anterior-posterior plane. Further, the halo could be attached to a plaster body cast or a vest type structure with supporting linkage to allow traction to continue while the patient ambulated. This mobility was the principal advantage of the halo ring, although another advantage existed in that there was no movement between the skull and fixation pins. This reduces the chance of infection of the scalp in the areas surrounding the pins.

Because the halo completely encircled the head, it was necessary during application that an assistant gently lift the head from the stretcher or support the head off the end of the table to provide sufficient space for the ring to be positioned around the patient's head.

Generally, the halo ring was placed just above the external ear. Pins were inserted through threaded holes spaced around the ring and diagonally opposite pins were tightened simultaneously using torque screwdrivers. The pins were then locked into place with set screws.

A disadvantage of the halo was that x-ray films of the pin location in the skull were difficult and deceptive, unless the x-ray was made of each pin at an angle tangential to the skull at the point of entry of the pin. The halo type ring also generally left pin hole scars over the eyebrows because the anterior placement of the pins was generally in the forehead region.

STATEMENT OF THE INVENTION

The orthopedic traction tong apparatus of this invention comprises the combination of a generally arcuate main support member which extends from one side to the other side, over the top of the head of the patient user of the device. Means located generally in the central portion of the arcuate support member are provided to apply tension at any predetermined angle, as measured with respect to an imaginary axis line extending vertically upward through the center of the head of the user patient when the tongs are in use, the vector angle being in the side-to-side relationship to the head of the user patient. The tension applying means also includes means for connecting the tongs to a source of tension at any predetermined angle, measured, when in use, with reference to the imaginary axis line, front-to-back of the head of the user patient.

A pair of pin support means are secured at each end of the arcuately configured main support member for securing cranial pins to the orthopedic traction tongs. Each of the pin support means comprising a generally arcuate member extending from an end of the main support member and partially around the head of the user patient for permitting cranial pins to be inserted into the skull at radially spaced intervals around the head of the user patient relationship of the main support means is thereby fixed with respect to the head of the user.

Means are also provided for securing fixation rods to respective ends of the main support and to fix the position of the traction tongs with respect to a vest or other external supporting means structure, thus enabling force to be applied through the rods to the main support means. Each rod connecting means comprises a pair of relatively rotatable clamp elements, and means for securing the clamp elements to each other in a fixed relationship for applying force and tension to the head of the user patient at a preselected angle.

The rod connecting means may be secured to the fixation rods at different positions on the respective side of the user's head, and thereby apply tension force through the tongs to the head at a preselected angle measured, when in use, with reference to an imaginary line from front-to-back of the head any force vector desired, front-to-back or side-to-side, or any force vector having both front-to-back and side-to-side components, may be applied through the traction tongs of the present invention to the patient's head.

DETAILED DESCRIPTION OF THE PREFERRED EMBODIMENT

Figure 1:
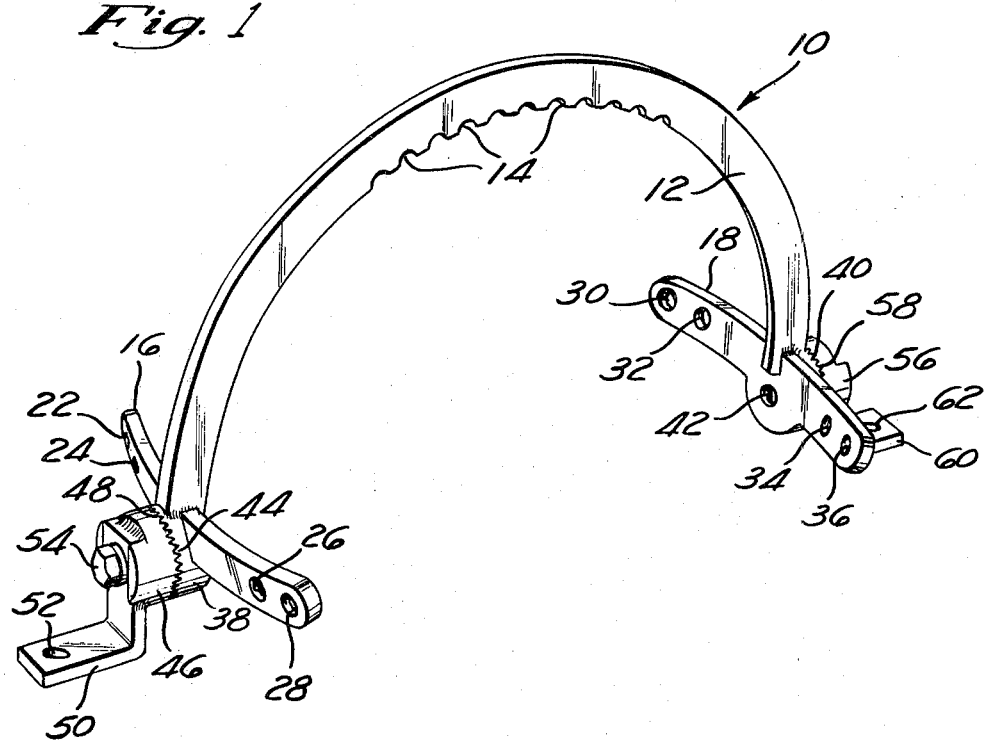
FIG. 1 is a perspective view of the orthopedic tongs of this invention, with the tension application means removed.

FIG. 1 of the drawings shows the overall configuration of an orthopedic traction tongs 10 of this invention, with the tension applying means removed for clarity of illustration.

The orthopedic traction tongs comprises a generally u-shaped main support means or member 12 which is generally in the configuration of a rigid arc. The main support means in the preferred embodiment is simply cut or stamped out of heavy metal plate and, typically, may be from ⅛ to ¼ inch in thickness and from ½ to 1 inch in width. These dimensions are not critical, so long as the main support means is generally rigid and is configured to extend from opposite sides of the patient's head over the top of the head.

Main support means 12 includes, in the exemplary embodiment, a plurality of notches 14 generally in the central area of the arcuate configuration thereof. These notches 14 coact with the tension applying means, which will be described in detail later, to apply force at a desired vector to the head of the patient. It is not essential to the invention that the notches be utilized. Indeed, the entire support-means frame may be smooth, provided that the tension-applying means is so constructed and configured as to be capable of being clamped tightly to any given position on the main support means. Other means of selectively attaching the tension applying means at any preselected position generally centrally of the main support member may also be used. The means including the notches and the tension support member to be described, however, provides the most convenient, reliable, and efficient connecting means presently contemplated.

A pair of pin support means 16 and 18 for securing cranial pins to the orthopedic traction tongs of this invention are secured at opposite ends of the main support means. Each pin support means comprises a slightly curved member extending forwardly and rearwardly from an end of the main support means to be generally parallel to the side of the patient's head. Each member supports one or more cranial pins for insertion into the skull at radially spaced intervals. Cranial pins of many types are known, and do not constitute a part of this invention. A particular and preferable cranial pin, however, is described and illustrated for convenience and completeness of disclosure.

In the preferred embodiment, externally threaded cranial pins manufactured by Wells, and sometimes referred to as Gardner-Wells pins, are used.

Pairs of threaded holes are provided adjacent opposite ends of each pin support means to receive the pins. Thus pin support means 16 has one pair of holes 22 and 24, and a second pair of holes 26 and 28 on opposite sides of the main support means. Similarly, pin support means 18 defines threaded holes 30, 32, 34, and 36. Obviously, it is not essential to provide threading, since the cranial pins could be locked into position with a pair of lock nuts or clamped into position by other means, but threading the holes 22 through 36 is a convenient and effective mechanism for permitting use of cranial pins to attach the orthopedic traction device in a fixed relationship on the patient's head.

Means are also provided for attaching the respective ends of the main support means to fixation rods. The use of fixation rods, per se, is well-known and is commonly used in connection with the aforementioned halo device. Lower ends of the fixation rods are commonly secured to a vest which fits tightly upon the user. The rods extend upwardly from the vest and are secured to the halo ring ring in a predetermined position with respect to an imaginary axis line (marked "A" in FIG. 5) extending upwardly through the center of the user's head.

In a comparable manner, the orthopedic traction tongs of this invention may be secured to the upper portion of such fixation rods. Similarly, when a patient is kept in a fixed position (for example, supine and immobile during initial adjustment of the spine and application of traction, or simply during traction, the orthopedic traction tongs of present invention may be secured to a fixation rod which is in turn secured to a bed or other supporting structure. Each rod connecting means includes means for securing the rods in a relationship so as to apply the force from the rods as tension to the head of the user patient at a preselected angle measured, when in use, with reference to the imaginary line extending upwardly from the center of the user's head, in the front-to-back direction of the head. In the preferred embodiment, these means comprise two pairs of relatively rotatable clamp elements. A first member of each pair, shown at 38 and 40 (FIGS. 1 and 6), respectively, is secured to the end of the main support frame. A threaded hole 42, and a corresponding threaded hole in element 38, which cannot be seen in the drawing, are provided. The outer side of the clamp element 38 is notched, as shown at 44, and mates with a relatively rotatable clamp element 46 which, as shown at 48, is notched in a mirror image configuration corresponding to the notching indicated at 44.

The clamp element 46 includes a rod connection portion 50 which, in the exemplary embodiment, includes a hole 52 to permit connection to the fixation rod on that side of the head. The clamp elements 38 and 46 may be relatively rotated when the bolt 54, is loose, but when the bolt 34 is tight, the two relatively rotatable elements are secured together in a fixed relationship, permitting the main support means to tilt to the front or to the back of the head of the user, when the device is in use, thereby applying force from the fixation rod as tension to the head of the user patient at a preselected angle in the front-to-back orientation of the user.

A like clamping bolt 55, relatively rotatable clamp element 56 with matched notching as shown at 58, and a rod attachment portion 60 with a hole 62 are provided on the other end of the main support means.

Figure 3:
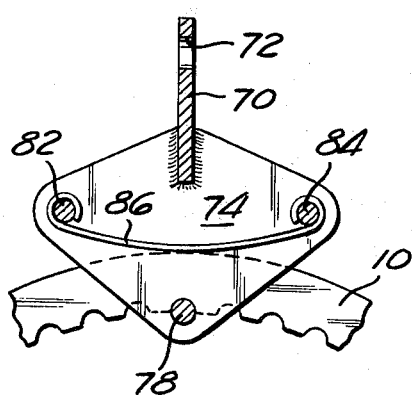
FIG. 3 is a cross-sectional view taken substantially along lines 3—3 in the direction of the arrows as shown in FIG. 2, showing the tension application means selectively movably secured at one position on the main arcuate support member.
Figure 2:
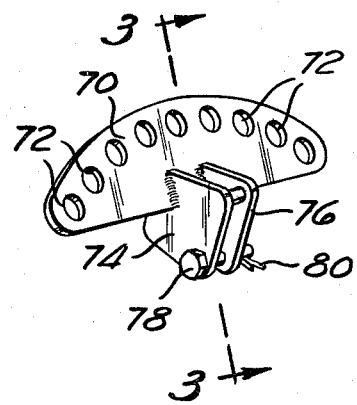
FIG. 2 is a perspective view of the tension application means.
Figure 4:
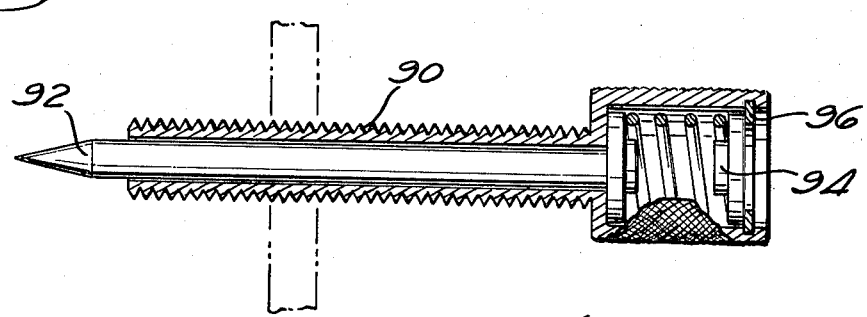
FIG. 4 is a cross-sectional view of a spring-loaded screw which may be used with the orthopedic tongs of this invention to attach the tongs to the head of the user patient.

FIG. 2 and FIG. 3 show, respectively, perspective and cross-sectional views of a tension applying means 70 which is positioned between the two ends of the main support member and is slidably received about the main support member. The tension applying means 70 comprises means such as a plate preferably having one edge in a generally arcuate configuration provided with a plurality of holes indicated generally at 72. As preferred, in an exemplary embodiment, the tension applying means also includes a pair of plates 74 and 76 welded to the plate 70 perpendicular thereto and spaced from each other. A bolt or pin 78 extends through holes in the lower part of the plates, and may be secured in place by pin 80, or by any other convenient means. As shown in FIG. 3, pin 78, when the device is in use, rests in one of the notches 14 in the main support means. It will be apparent that the tension applying means may be centered on, or positioned on either side of center of the main support means.

Also in the preferred embodiment, a pair of pins 82 and 84, extend between plates 74 and 76 on opposite sides of plate 70. A resilient leaf spring 86 is positioned between plates 74 and 76, and is supported by pins 82 and 84 which fit through looped ends of the spring. When it is desired to move the tension applying means from one preselected position to another, the tension applying means is simply pressed downwardly, as viewed in FIG. 3, causing the leaf spring 86 to flex and removing the pin 78 from the respective notch 14 permitting the tension applying means to be conveniently and easily slid in a generally arcuate path along the main support means. When the downward force is removed, the leaf spring causes the pin 78 to engage the bottom of the main support means and, when properly positioned, to engage in one of the notches 14 again.

The leaf spring 86, when attached as described, and the pin 78, as described, constitute means for selectively attaching the tension applying means at any preselected position generally centrally of the main support member for applying tension, when the orthopedic traction tongs are in use, at a preselected angle measured with reference to the imaginary axis line extending upwardly through the center of the user's head, side-to-side of the head of the patient. The holes 72 constitute means for connecting the tension applying means to a source of tension at predetermined angle, measured, when the device is in use, with reference to the imaginary axis line as described, in the front-to-back direction relatively to the head of the user patient.

By using the two attaching means just described, the means for selectively attaching tension applying means in the side-to-side position relatively to the head of the user and the means for connecting the tension applying means to a source of tension, for applying tension in the front-to-back direction, relatively to the head of the user, either of these or a combination of these vectors, i.e., side-to-side or front-to-back may be used. For example, the head of the user may be inclined forwardly and to the left, or rearwardly and to the left, by the application of the tension force which, of course, is transmitted from the head of the user to the spine. The force vector of the tension may, therefore, be applied at any predetermined angle in which the head of the user may be oriented.

The Wells cranial pins, with which this particular invention is adapted for use, comprise a hollow cylindrical element 90 having a hollow head. A pin 92, generally in the configuration of a headed nail, i.e., with a point on one end and with a head at the other end, is slidably received in the hollow interior of the externally threaded element 90. A compression coil spring 94 rests against the head of the pin 92 and is maintained in the hollow head of the element 90 by a keeper ring 96. In use, the pin 92 is forced toward and into the skull of the patient by twisting the head of element 90, which being threadably received in the pin support means forces the pin 92 toward the skull. Upon application of a predetermined force, as determined by the force required to compress the spring 94, further turning of element 90 does not force the pin into the skull of the patient but, rather, causes compression of the spring 94. Other pins, may be used, but the present invention is very conveniently used with the above described Wells pin.

Figure 5:
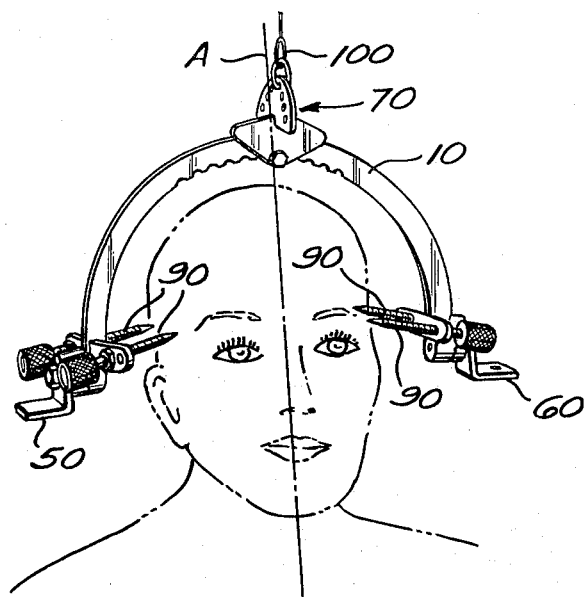
FIG. 5 is a perspective view of the orthopedic traction tongs of this invention in use, the patient's head being in phantom line, and showing an imaginary axis line extending vertically upwardly through the center of the head for reference in measuring the vector angle for application of the tension force to the head, and thus to the patient's spine.

FIG. 5 depicts the orthopedic traction tongs of this invention in position on the head of the user patient, the head being shown in phantom lines, and connected to a tensioned line 100 which is a source of tension force.

For reference in measuring the vector angle of the force supplied to the head of the user, axis line A, which is an imaginary line extending upwardly through the center of the head of the user, is shown.

The main support means 12 of a rigid arcuate construction extends from one side of the user's head over the top to the other side of the head. The pair of pin support means (16 and 18) for securing cranial pins to the orthopedic traction tongs are connected, respectively, at the ends of the main support means and comprise generally arcuate members extending from the ends of the main support means, partially around the head permitting the cranial pins 92 to be inserted into the skull at radially spaced intervals. Tension applying means 70 is positioned between the two ends of, and slidably mounted on, the main support member. The means for selectively attaching the tension applying means at any preselected position generally centrally of the main support member, comprises the pin 78 and the notches 14 as previously described. When the device is in use, tension force may thereby be applied at any preselected angle, as measured with reference to the imaginary axis line A, in the side-to-side direction with reference to the head of the user patient, by positioning the tension applying means on either side of the axis A.

Rod connecting means, including the rod connecting portions 50 and 60, are also provided for securing the respective ends of the main support means to fixation rods. In FIG. 5, these rod connecting means are not used, and the tension force supplied to the head, and consequently to the spine, comes entirely through line 100 which may be attached through holes 72 of the tension applying means 70 in any position, in the front-to-back orientation of the user's head, for connection to the source of tension at any predetermined angle which is measured, when the device is in use, with reference to the imaginary axis line, front-to-back, to apply the tension force in the desired vector frontwardly or backwardly of the head of the user. Clearly, the tension applying means may be attached, for example, to the right, as shown in FIG. 5 of center of the main support means, and line 100 may be connected in a hole 72 in the front of the plate 70 of the tension supplying means, as viewed in FIG. 5, thereby applying the tension force in a vector to the right and to the rear of the axis A of the user patient.

Figure 6:
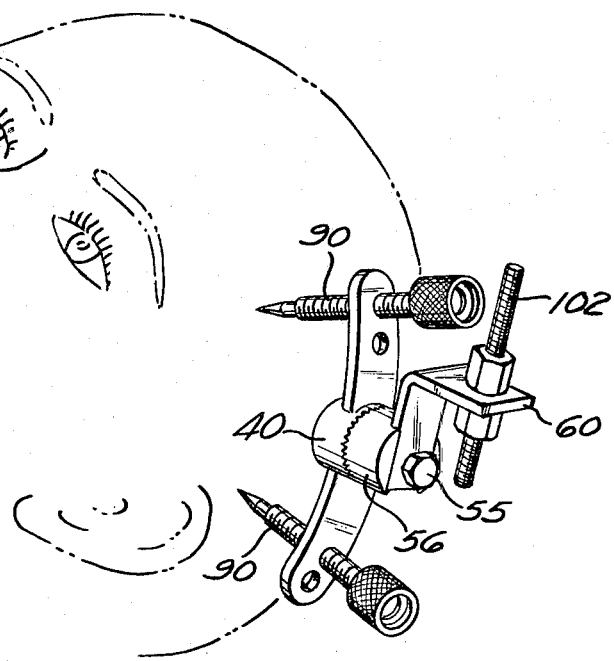
FIG. 6 is a detailed perspective view of the rod connecting means of this invention, and the positioning of cranial pins in the pin supporting means the patient's head being shown in phantom line.

The threaded end of a fixation rod 102 or a bolt connected to the fixation rod is shown, in FIG. 6, secured to the rod connecting means, by means of the portion 60. The head of the user patient is secured to the main supporting means by means of the cranial pins 90. The orientation of the relatively rotatable clamp elements 40 and 56, is secured by bolt 55. Thus, without moving fixation rod 102, the head of the user patient may be tilted forwardly or backwardly so as to apply the force from the fixation rod as tension through the main tension applying means at any desired vector angle, in the front-to-back orientation, with respect to the imaginary axis line A, which is shown in FIG. 5.

The orthopedic traction tongs of this invention are shown as described with reference to the preferred and exemplary embodiment, but the invention is not limited to this specific embodiment. For example, virtually any type of rod connecting means which include a pair of relatively rotatable clamp elements and means for securing the clamp elements to each other in a fixed relationship, and means for connecting the fixation rods thereto, may be regarded as equivalent in the context to the overall, combinational features of the invention. Likewise, any means which permits the tension aplying means to be connected, clamped or secured selectively along the arcuate configuration of the main support means, may be regarded as equivalent in the overall combinational features of the invention. Means which will permit the application of force in a frontwardly or backwardly orientation, with respect to the imaginary axis line used as a reference, may be regarded as equivalent when found in the overall combination of the invention. The main support means is shown and described as a generally arcuate flat element. This is, of course, a very straight forward and simple configuration for this element of the invention but any support means which permits the tension applying means to be connected thereto generally along an arcuate path may be used. Likewise, while the configuration is decribed as an arc or in an arcuate configuration, there is no criticality to the arc and it need not be a circular arc. Other variations may also be made departing from the spirit and scope of the invention.

What is claimed is:

1. Orthopedic traction tongs for applying tension at selected vector angles, measured with reference to an imaginary axis line extending vertically upwardly through the center of the head of a user patient when the tongs are in use, for being attached to the head of the user patient when in use by cranial pins, comprising the combination of:

main support means generally in the configuration of a rigid arc so constructed and configured as, when in use, to extend from side of the user patient's head over the top to the other side of the user patient's head;

a pair of pin support means for securing cranial pins to the orthopedic traction tongs, each pin support means comprising a generally arcuate member extending from the ends of the main support means, when in use, partially around the head of the user patient for permitting cranial pins to be inserted into the skull of the user patient at radially spaced intervals;

tension applying means positioned between the two ends of and on the main support member;

means for selectively attaching the tension applying means at any preselected position generally centrally of the main support member, for applying, when in use, tension at a preselected angle, measured with reference to the imaginary axis line, side-to-side and front-to-back of the head of the user patient; and rod connecting means secured to the respective ends of the main support means for securing fixation rods to the traction tongs for applying force through said rods to said main support means, said rod connecting means each comprising a pair of relatively rotatable clamp elements and means for securing said clamp elements to each other in a fixed relationship for thereby applying said force as tension to the head of the user patient at a preselected angle measured, when in use, with reference to said imaginary line from front-to-back of the head of the user patient.

* * * * *

UNITED STATES PATENT AND TRADEMARK OFFICE
CERTIFICATE OF CORRECTION

PATENT NO. : 4,444,179
DATED : April 24, 1984
INVENTOR(S) : Anthony C. Trippi

It is certified that error appears in the above-identified patent and that said Letters Patent is hereby corrected as shown below:

```
Col. 1, line 11, change "signal" to -- spinal --.
Col. 3, line 17, after "head" delete "of the user patient"
                 and add -- . --.
Col. 3, line 17, before "relationship" add -- The --.
Col. 3, line 22, after "support" delete "and" and substitute
                 -- member --.
Col. 3, line 36, change "any" to -- Any --.
Col. 3, line 67, after "means" insert -- , --.
Col. 5, line 4, after "ring" (first occurrence) insert
                 -- , fixing the --.
Col. 5, line 13, after "traction" (second occurrence) insert
                 -- ) --.
Col. 5, line 38, after "54" delete ",".
Col. 5, line 39, change "34" to -- 54 --.
Col. 7, line 47, before "or" insert -- ( --.
Col. 7, line 48, after "rod" insert -- ) --.
Col. 8, line 4, change "aplying" to -- applying --.
Col. 8, line 22, after "made" add -- without --.
```

Signed and Sealed this

Twenty-ninth Day of January 1985

[SEAL]

*Attest:*

DONALD J. QUIGG

*Attesting Officer*   *Acting Commissioner of Patents and Trademarks*